US011484220B2

(12) United States Patent
Mei et al.

(10) Patent No.: US 11,484,220 B2
(45) Date of Patent: *Nov. 1, 2022

(54) SURGICAL EQUIPMENT CONTROL INPUT VISUALIZATION FIELD

(71) Applicant: INTUITIVE SURGICAL OPERATIONS, INC., Sunnyvale, CA (US)

(72) Inventors: Yiming Mei, Fremont, CA (US); Michael Ikeda, Saratoga, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 407 days.

This patent is subject to a terminal disclaimer.

(21) Appl. No.: 16/703,497

(22) Filed: Dec. 4, 2019

(65) Prior Publication Data
US 2020/0107749 A1    Apr. 9, 2020

Related U.S. Application Data

(63) Continuation of application No. 14/785,726, filed as application No. PCT/US2014/035258 on Apr. 24, 2014, now Pat. No. 10,542,908.
(Continued)

(51) Int. Cl.
*A61B 5/06*    (2006.01)
*B25J 9/16*    (2006.01)
(Continued)

(52) U.S. Cl.
CPC .......... *A61B 5/065* (2013.01); *A61B 1/00045* (2013.01); *A61B 1/00193* (2013.01);
(Continued)

(58) Field of Classification Search
CPC . A61B 5/065; A61B 1/00045; A61B 1/00193; A61B 34/30; A61B 34/37; A61B 90/361; A61B 2017/00973; A61B 2018/00982; A61B 2090/371; A61B 2090/372; B25J 9/1689; G05B 2219/40169; G05B 2219/40195
See application file for complete search history.

(56) References Cited

U.S. PATENT DOCUMENTS 6,852,107 B2    2/2005 Wang et al.
8,120,301 B2    2/2012 Goldberg et al.
(Continued)

OTHER PUBLICATIONS

International Search Report and Written Opinion for Application No. PCT/US14/35258, dated Aug. 26, 2014, 12 pages.
(Continued)

*Primary Examiner* — Peter Luong
(74) *Attorney, Agent, or Firm* — Artegis Law Group, LLP

(57) ABSTRACT

A control console includes a first input control operable by an operator and outside of a field of view of the operator, a display within the field of view of the operator, and a first image capture device. The first image capture device acquires a first image of a physical environment surrounding the first input control and at least part of the first input control. The first image is output on the display. In some embodiments, a second image of a work site may also be displayed, so that the operator can locate and operate the first input control while continuously viewing the second image of the work site.

20 Claims, 6 Drawing Sheets

Related U.S. Application Data

(60) Provisional application No. 61/815,973, filed on Apr. 25, 2013.

(51) Int. Cl.
| | | |
|---|---|---|
| *A61B 34/30* | (2016.01) | |
| *A61B 34/37* | (2016.01) | |
| *A61B 1/00* | (2006.01) | |
| *A61B 17/00* | (2006.01) | |
| *A61B 90/00* | (2016.01) | |
| *A61B 18/00* | (2006.01) | |

(52) U.S. Cl.
CPC .............. *A61B 34/30* (2016.02); *A61B 34/37* (2016.02); *B25J 9/1689* (2013.01); *A61B 90/361* (2016.02); *A61B 2017/00973* (2013.01); *A61B 2018/00982* (2013.01); *A61B 2090/371* (2016.02); *A61B 2090/372* (2016.02); *G05B 2219/40169* (2013.01); *G05B 2219/40195* (2013.01)

(56) References Cited

U.S. PATENT DOCUMENTS

| | | |
|---|---|---|
| 10,542,908 B2 | 1/2020 | Mei et al. |
| 2009/0088772 A1 | 4/2009 | Blumenkranz |
| 2011/0118753 A1 | 5/2011 | Itkowitz et al. |
| 2012/0071892 A1 | 3/2012 | Itkowitz et al. |

OTHER PUBLICATIONS

Sim H.G., et al., "Equipment and Technology in Surgical Robotics," World Journal of Urology, 2006, vol. 24 (2), pp. 128-135.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

SURGICAL EQUIPMENT CONTROL INPUT VISUALIZATION FIELD

RELATED APPLICATIONS

This application is a continuation of U.S. patent application Ser. No. 14/785,726, filed Oct. 20, 2015, which is the U.S. national phase of International Application No. PCT/US2014/035258, filed Apr. 24, 2014, which designated the U.S. and claims priority to U.S. provisional patent application 61/815,973, filed on Apr. 25, 2013, the contents of each of which are incorporated herein by reference.

TECHNICAL FIELD

The present disclosure is directed to systems and methods for surgery, and more particularly to systems and methods for providing clinicians with viewing of a surgical site and a medical equipment control component outside his field of view.

BACKGROUND

It is a primary objective of surgery, whether open or through the use of minimally invasive techniques, to reduce the duration of the procedure and minimize blood loss, the risk of infection, and other bad side effects. With the advent of new surgical equipment, additional equipment and technologies are incorporated into the procedure with the primary purpose of improving the efficacy of the procedure. Incorporation of new equipment and technologies into procedures sometimes complicates things by requiring the surgeon to access additional control components. In open surgery, the surgeon's field of view typically includes only the surgeon's hands and not the surgeon's feet. Alternatively, during minimally invasive surgery, the surgeon's attention is typically focused on a video display of the surgical site. Here, the surgeon's own hands and the control components they operate are likely outside his or her field of view. If the surgeon seeks to locate a control component outside his field of view, the surgery must be interrupted, however briefly, to permit the surgeon to turn away from the surgical site. Such interruptions and distractions disturb surgical work flow, and increased procedure duration or even patient harm may result. Improved systems and methods are needed to allow a surgeon to easily access various surgical equipment control components while minimizing impact on surgical work flow.

SUMMARY

The present invention provides systems and methods for medical persons to view surgical equipment control components outside his or her field of view during surgery. The systems provided include an image capture device and a display coupled to the image capture device. The image capture device is configured to capture within its field of view part of a surgical equipment control component. This image captured by the image capture device is output by the display. The display is positioned within the field of view of the medical person operating the surgical equipment control component.

The methods provided involve capturing an image containing part of a surgical equipment control component and part of the body part of the medical person used to operate the surgical equipment control component. The captured image is then displayed to the medical person operating the surgical equipment control component.

BRIEF DESCRIPTIONS OF THE DRAWINGS

Aspects of the present disclosure are best understood from the following detailed description when read with the accompanying figures. Various features are not drawn to scale. The dimensions of the various features may be arbitrarily increased or reduced for clarity of discussion.

Figure 5A:
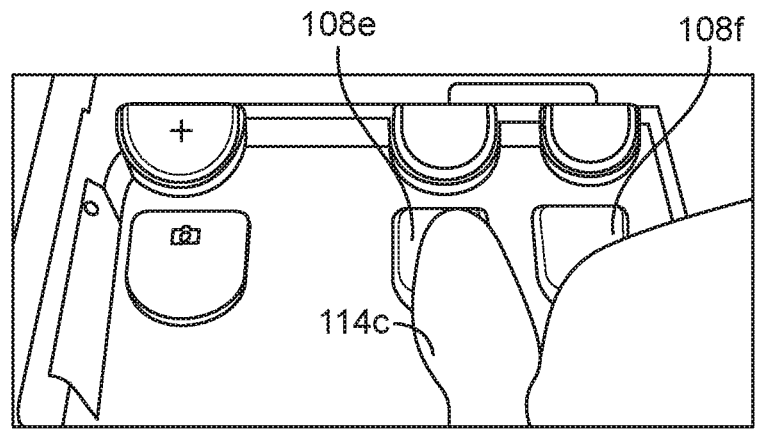
Figure 5B:
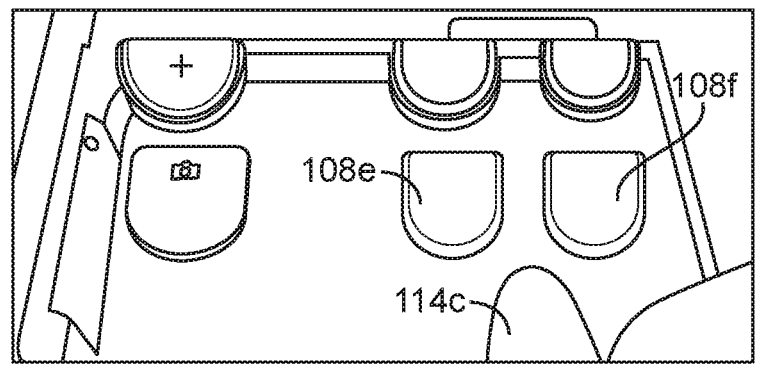
Figure 5C:
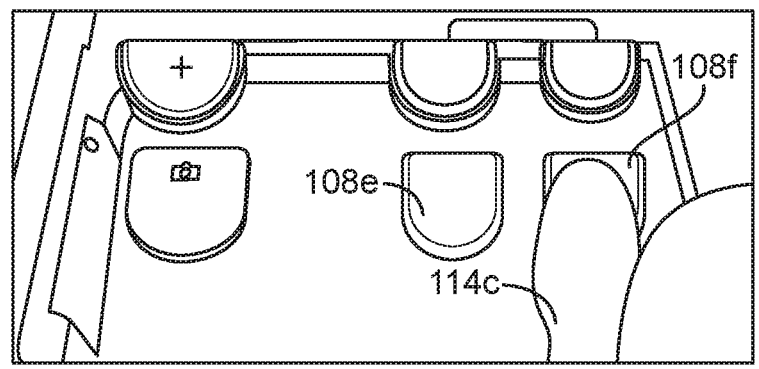

FIGS. 5A, 5B, and 5C are perspective views that illustrate a surgeon's foot on various foot pedals.

Figure 6:
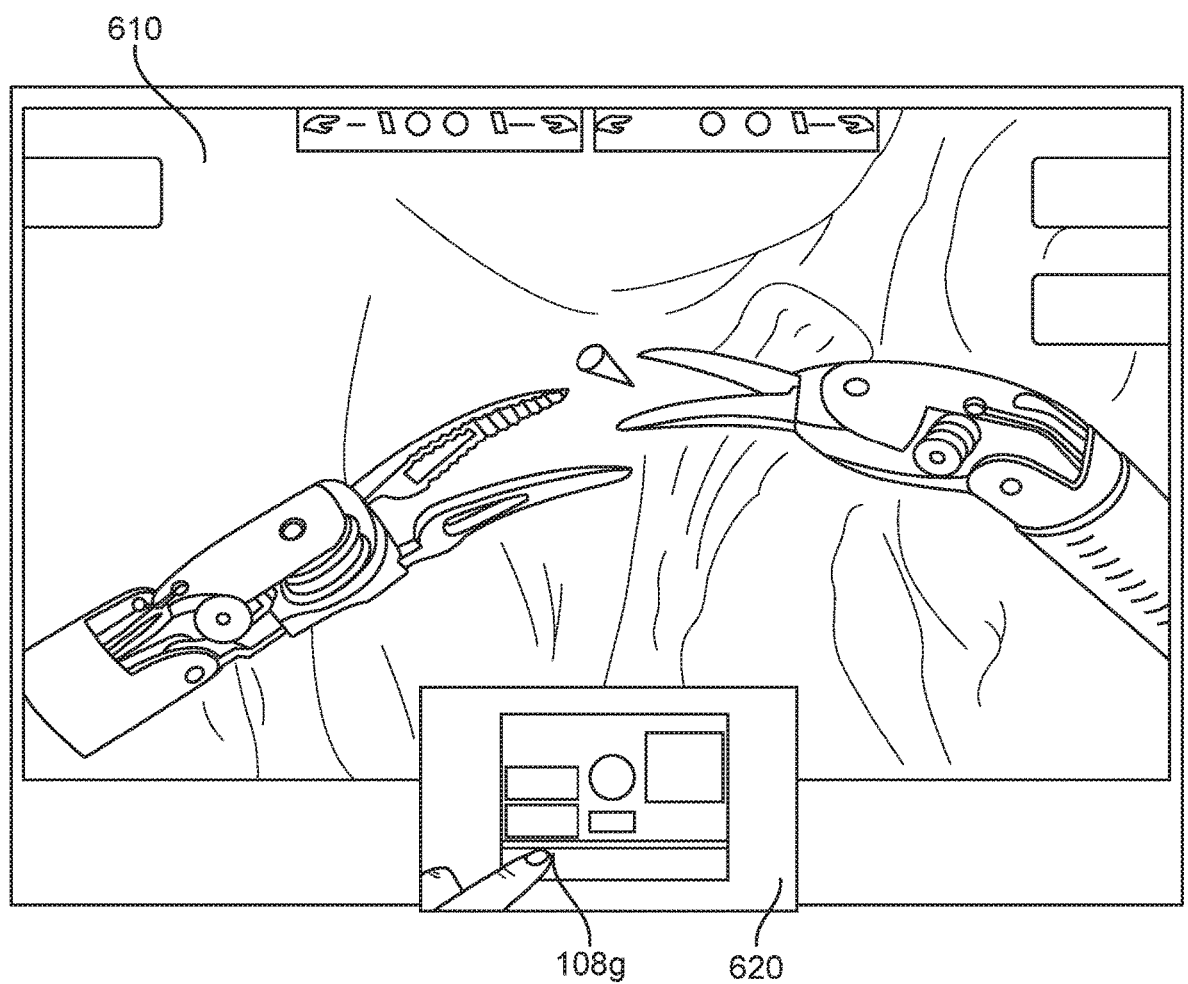

FIG. 6 is an image of the surgical site and an image of the touch-sensitive control interface, output on a single display.

DETAILED DESCRIPTION

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci™ Surgical System (specifically, a Model IS3000, marketed as the da Vinci™ Si™ HD™ Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci™ Surgical Systems (e.g., the Model IS3000; the Model IS2000, commercialized as the da Vinci™ S™ HD™ Surgical System) are merely exemplary and are not to be considered as limiting the scope of the inventive aspects disclosed herein.

Figure 1:
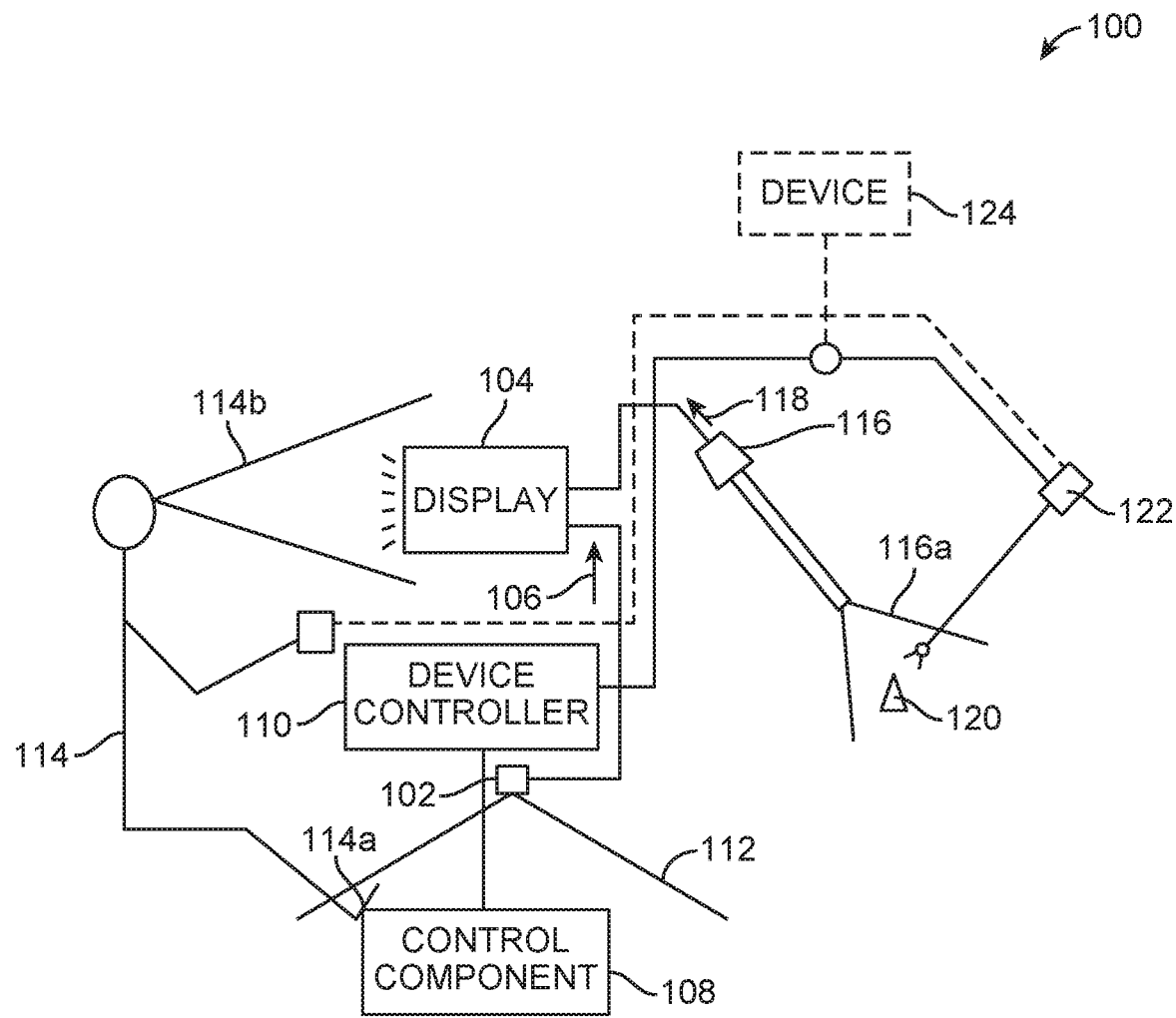
FIG. 1 is a diagrammatic view of display system components.

FIG. 1 is a diagrammatic view of a display system 100. Display system 100 includes an image capture device 102 and a display 104 coupled to capture and output moving visual (video) images 106 from image capture device 102. Image capture device 102 is positioned so that a control component 108 for a surgical equipment device controller 110 is within image capture device 102's field of view 112. Image capture device 102 may be monoscopic or stereoscopic.

As shown in FIG. 1, a medical person 114 (e.g., a surgeon or other medically trained person) operates control component 108. FIG. 1 shows person 114 operating control component 108 with a foot 114a, which is illustrative of various ways to operate the control component (e.g., with a hand, finger, elbow, knee, etc.). Display 104 is positioned so that images 106 from image capture device 102 are output within person 114's field of view 114b.

FIG. 1 also shows a surgical image capture device 116 positioned to capture and output moving visual images 118 of a surgical site 120, which is within surgical image capture device 116's field of view 116a. For minimally invasive surgery implementations, surgical image capture device 116 is an endoscope (mono- or stereoscopic). Moving visual images 118 are received and output by display 104. Consequently, in some aspects person 114 simultaneously views both images 106 and images 118, as described in more detail below. Where such simultaneous viewing is desired, it should be appreciated that as an alternative to images 106 and images 118 both being received and output by display 104, an additional display (not shown) positioned within person 114's field of view 114b may be used. In such aspects, images 106 or images 118 are received and output by display 104, and the images 106,118 not received and output by display 104 are received and output by the additional display (not shown) so that both images 106 and images 118 are output within person 114's field of view 114b.

In some aspects, surgical equipment device controller 110 controls a feature of a device 122 at the surgical site 120. For example, device 122 may be an electrosurgical instrument, and so surgical equipment device controller 110 is an electrosurgical energy generator that is coupled to route electrosurgical energy (e.g., for cutting, for cautery, and the like) to device 122. In this example, control component 108 functions as an on/off control for the electrosurgical generator, so that person 114 can control application of electrosurgical energy at the surgical site. The electrosurgical energy function is merely illustrative, and various other surgical functions can be similarly controlled, such as suction, irrigation, other tissue fusing functions, tissue stapling functions, endoscopic camera control and illumination functions, robotic master/slave control functions, etc. Similarly, and as an alternative by dashed line, surgical equipment device controller 110 may control equipment 124 that does not directly affect the surgical site. Examples of such equipment 124 include operating room environment functions, patient data display functions, and any other function a surgeon may want to directly control via control component 108 while performing surgery.

Since the operating room environment may include more than one control component 108, various combinations of one or more image capture devices 102 may be used to capture images of the various control components. For instance, an image of two or more control components 108 may be captured in a single image capture device 102's field of view. Alternatively, an image of one or more control components 108 may be captured in one image capture device 102's field of view, and another image of one or more additional control components 108 may be captured in another image capture device 102's field of view. And, an image of a control component 108 may be captured in two or more image capture devices' 102 fields of view. Consequently, in implementations that include two or more image capture devices 102, one, two, or more corresponding images can be output at display 104.

FIG. 1 further illustrates that person 114 may control device 122 at the surgical site in various ways, represented by dashed line. In one aspect, device 122 is a manually operated surgical instrument that person 114 directly operates. Since at least a portion of device 122 is within image capture device 116's field of view 116a, person 114 sees both device 122's motion and the person 114's physical relation to control component 108 in display 104. Alternatively, in other aspects, person 114 operates a telesurgical robotic master control component (not shown), and device 122 is a surgical instrument robotically slaved to follow telesurgical robotic master control component's motion and other optional control inputs.

In one aspect, additionally or as an alternative to image capture device 102, display system 100 includes one or more sensors (e.g., infrared beam detectors) positioned to acquire information about the physical environment of control component 108. Display system 100 uses information acquired by the one or more sensors to create a computer-generated representation showing control component 108 and its interaction(s) with its immediate surroundings. In one aspect, control component 108 is operated by person 114's foot. Infrared beam detectors positioned on and/or around control component 108 detect the position of person 114's foot as it moves towards and away from control component 108. A computer-generated representation of this information is displayed to person 114 on display 104.

Figure 2:
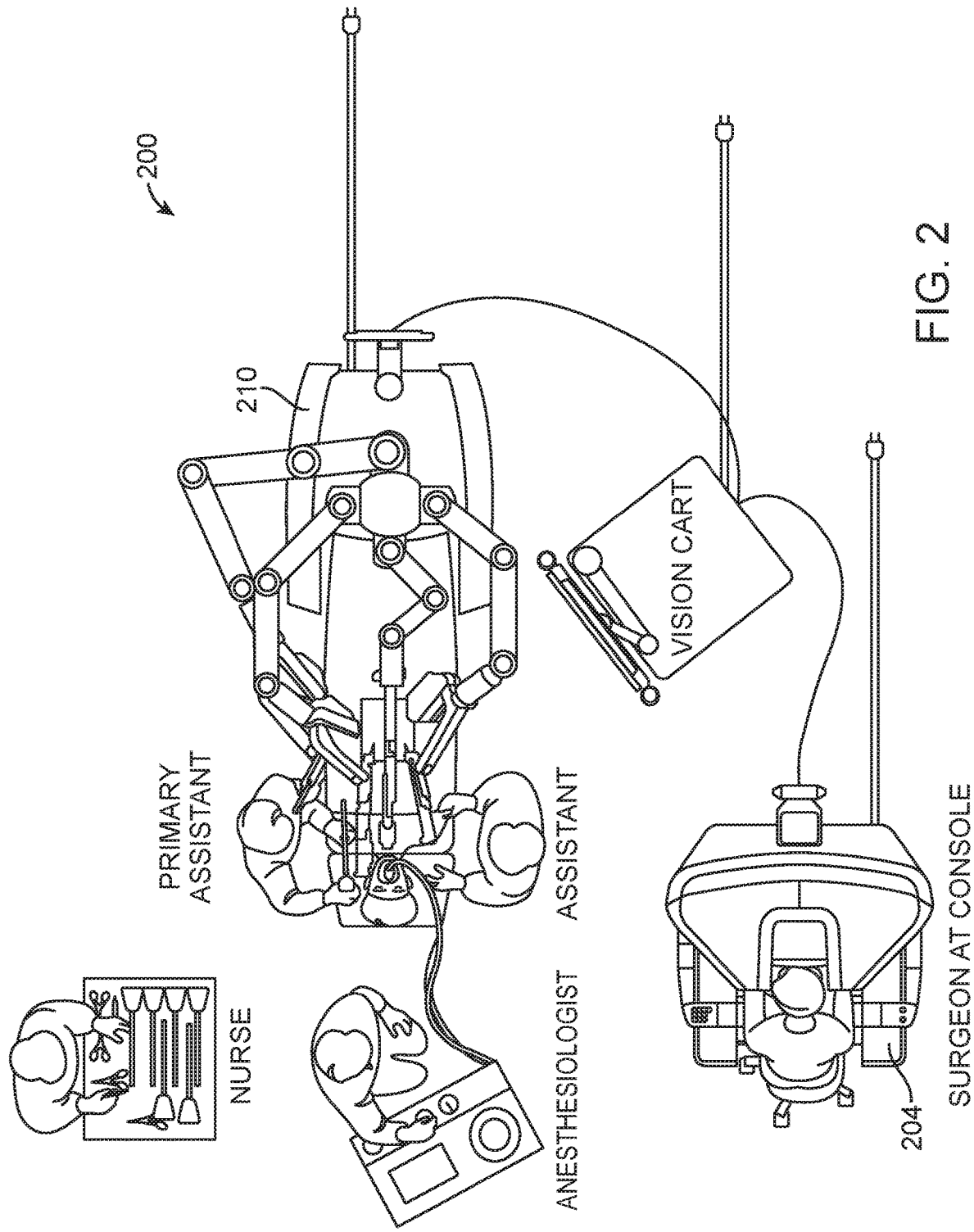
FIG. 2 is a plan view of a telesurgical robotic system.
Figure 3:
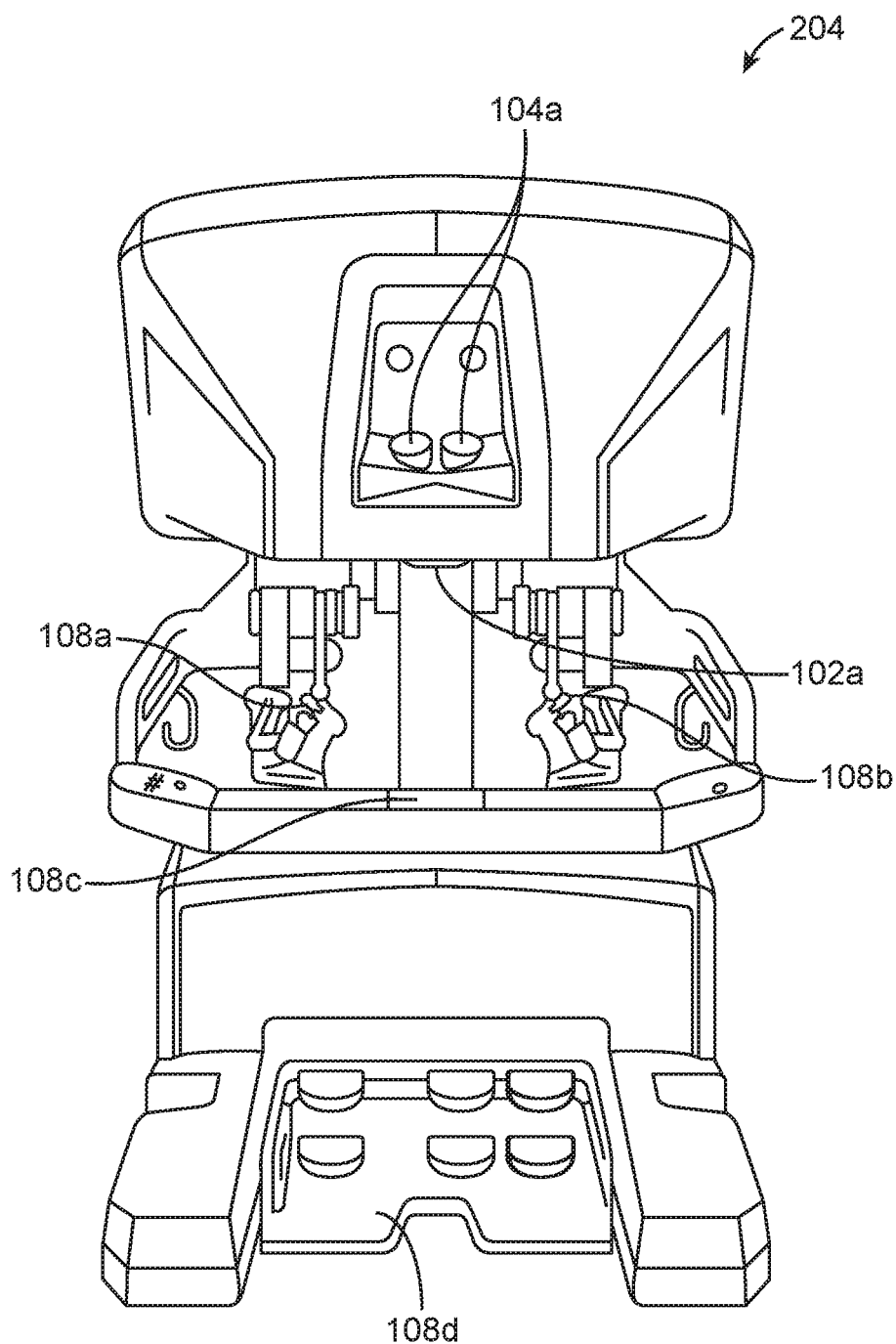
FIG. 3 is a front elevation view of a master control console in a telesurgical robotic system.

FIG. 2 is a plan view of a telesurgical robotic system 200 used to perform minimally invasive surgery. The telesurgical robotic system 200 includes a master control console 204 and a robotic slave device manipulator cart 210. FIG. 3 is a front elevation view of a master control console 204. The master control console 204 includes a control console stereoscopic display 104a. The control console stereoscopic display 104a is coupled to a stereoscopic endoscope (not shown; see FIG. 4, element 116b) that is configured to capture an image of the surgical site. The master control console 204 also includes a left telesurgical robotic master control component 108a, a right telesurgical robotic master control component 108b, a foot pedal assembly 108d, a touch-sensitive display control interface 108c, and a control component image capture device 102a. The control component image capture device 102a may be monoscopic or stereoscopic.

During use of the telesurgical robotic system 200, an operator seated at the master control console 204 operates one or more telesurgical robotic master control component(s) 108a,108b to control the movement of one or more corresponding surgical instruments robotically slaved to follow the motion of the corresponding telesurgical robotic master control component. The operator's control of the robotically slaved surgical instruments (not shown; see FIG. 4, element 122a; see also FIG. 1, element 122) is facilitated by the video image of the surgical site (not shown; see FIG. 6, element 610) captured by the stereoscopic endoscope (not shown; see FIG. 4, element 116b; see also FIG. 1, element 116) that is received and output to the operator by the control console stereoscopic display 104a.

Figure 4:
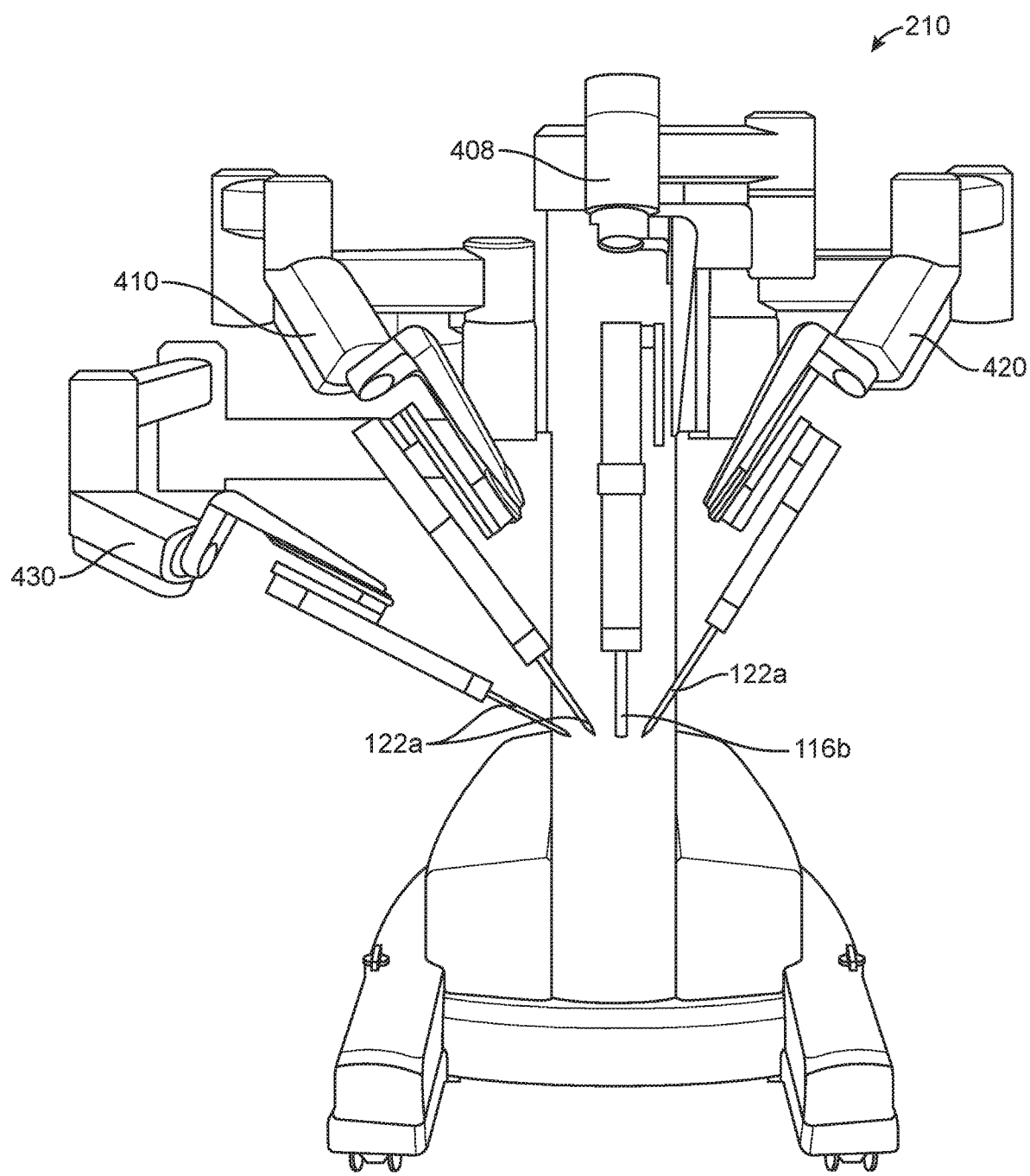
FIG. 4 is a front elevation view of a robotic slave device manipulator cart in a telesurgical robotic system.

FIG. 4 is a front elevation view of a robotic slave device manipulator cart 210. The robotic slave device manipulator cart 210 includes an endoscope manipulator 408, a first instrument manipulator 410, a second instrument manipulator 420, and a third instrument manipulator 430. The endoscope manipulator 408 is configured to allow a stereoscopic endoscope 116b (see also FIG. 1, element 116) to be releasably coupled. The first instrument manipulator 410, the second instrument manipulator 420, and the third instrument manipulator 430 are each configured to allow a robotically slaved surgical instrument 122a (see also FIG. 1, element 122) to be releasably coupled and operated.

During use of telesurgical robotic system 200, the stereoscopic endoscope 116b is configured to capture within its field of view the surgical site and the parts of the robotically slaved surgical instruments 122a manipulating tissue at the surgical site. The stereoscopic endoscope 116b is coupled to the control console stereoscopic display 104a, thereby enabling the control console stereoscopic display 104a to receive the surgical site image captured by the stereoscopic endoscope 116b and output the image to the operator of telesurgical robotic system 200.

Referring to FIG. 3, as discussed above, the master control console 204 includes a touch-sensitive display control interface 108c and a foot pedal assembly 108d. The touch-sensitive display control interface 108c and the foot pedal assembly 108d provide the operator of the telesurgical robotic system 200 with access to a variety of control components. Some of these control components may control surgical functions that directly affect the surgical site such as suction, irrigation, tissue fusing functions, tissue stapling functions, endoscopic camera control and illumination functions, robotic master/slave control functions, etc. Other control components may control functions that do not directly affect the surgical site, such as operating room environment functions, patient data display functions, or any other function a surgeon may want to directly control while performing surgery.

During normal operation of the telesurgical robotic system 200, the operator of the telesurgical robotic system 200 operates the left telesurgical robotic master control component 108a using the left hand and the right telesurgical robotic master control component 108b using the right hand to control corresponding robotically slaved instruments 122a located at the surgical site. The operator's actions are facilitated by the surgical site image captured by the stereoscopic endoscope 116b, which is received by the control console stereoscopic display 104a and output to the operator. A consequence of the telesurgical robotic system 200 operator viewing the surgical site image on the stereoscopic display 104a, however, is that the operator's field of view is generally limited to the field of view of the stereoscopic endoscope 116b capturing the surgical site image. If the operator of the telesurgical robotic system 200 seeks to operate a control component that his or her corresponding operating body part has not yet located (e.g., a hand-operated control component located on the touch-sensitive display control interface 108c, a foot-operated control component that is not located immediately beneath the operating foot, etc.), he or she generally must look away from the surgical site image output on the control console stereoscopic display 104a to locate and actuate this control component.

It should be appreciated that it is desirable to minimize the extent to which the operator of the telesurgical robotic system 200 is required to divert his attention from the surgical site when he seeks access to control components located on the touch-sensitive display control interface 108c, on the foot pedal assembly 108d, or at any other location accessible to the operator while the operator is seated at the master control console 204. In accordance with some aspects, a control component image capture device 102a (mono- or stereoscopic) is coupled to the control console stereoscopic display 104a and is configured to capture within its field of view a control component accessible to the operator of the telesurgical robotic system 200. Both the control component image captured by the control component image capture device 102a and the surgical site image captured by the stereoscopic endoscope 116b are received and output by the control console stereoscopic display 104a. It should be appreciated that the control component image and the surgical image may be displayed concurrently on the stereoscopic display 104a or alternatively be displayed one at a time.

In some aspects, the control component image capture device 102a is configured to capture within its field of view a control component and the control component's surroundings. In these aspects, the operator of the telesurgical robotic system 200 is able to view the physical relation between the operator's body part used to actuate the control component and the control component itself as the operator's body part approaches and/or moves away from the control component. As discussed earlier, control component image capture device 102a may be monoscopic or stereoscopic. If stereoscopic, the corresponding depth sensation from the image displayed to the operator helps the operator position the operating body part on the control component. As an example, the ability of the telesurgical robotic system 200 operator to view on the control console stereoscopic display 104a the relation between the operator's feet and various foot-operated control components located on the foot pedal assembly 108d facilitates the operator's repositioning of his feet to actuate the various foot-operated control components during a surgical procedure without looking away from the control console stereoscopic display 104a, and correspondingly the surgical site image displayed thereupon.

FIGS. 5A, 5B, and 5C are perspective views showing illustrative control components located on the foot pedal assembly 108d, including a first right foot control component 108e and a second right foot control component 108f. Also shown is part of the telesurgical robotic system 200 operator's right foot 114c. FIG. 5A shows the operator's right foot 114c actuating the first right foot control component 108e. FIG. 5B shows the operator's right foot 114c as it moves away from the first right foot control component 108e and approaches the second right control component 108f. FIG. 5C shows the operator's right foot 114c actuating the second right foot control component 108f. In this example, the first right foot control component 108e functions as an on/off control for the electrosurgical generator, controlling the application of electrosurgical energy delivered to the tip of a robotically slaved surgical instrument (not shown; see FIGS. 1 and 4) coupled to the left telesurgical robotic master control component 108a. The second right foot control component 108f also functions as an on/off control for the electrosurgical generator, controlling application of electrosurgical energy delivered to the tip of a robotically slaved surgical instrument coupled to the right telesurgical robotic master control component 108b. As discussed earlier, it should be appreciated that in some aspects, the foot-operated control components control functions other than electrosurgical functions. As discussed above, these foot-operated control components may control surgical functions that directly affect the surgical site such as suction, irrigation, tissue fusing functions, tissue stapling functions, endoscopic camera control and illumination functions, robotic master/slave control functions, etc. Other foot-operated control components may control functions that do not directly affect the surgical site such as operating room environment functions, patient data display functions, or any other function a surgeon may want to directly control while performing surgery. It should also be appreciated that in some aspects, the control component image capture device 102a captures within its field of view control components operated by a body part not the operator's right foot 114c. In this example, use of a right foot 114c to operate a control component is merely illustrative, as the body part used by the telesurgical robotic system 200 operator depends on the physical relation between the operator's body and the control component. In some aspects, the control component captured within the field of view of the control component image capture device 102a is positioned to be actuated by the operator's left foot, the operator's hand(s), the operator's elbow(s), etc. For example, the control component image capture device 102 may be configured to capture within its field of view an image containing one or more telesurgical robotic master control component(s) 108a, 108b and the immediate surroundings, to be displayed by control console stereoscopic display 104a.

In accordance with some aspects, FIG. 6 is an image as viewed from the control console stereoscopic display 104a, and it includes a surgical site image 610 received from the stereoscopic endoscope 116b and a control component image 620 received from the control component image capture device 102a. As shown in FIG. 6, the surgical site image 610 and the control component image 620 may be concurrently output by the control console stereoscopic display for viewing by the operator of the telesurgical robotic system. In this example, the control component image capture device 102a is configured to capture within its field of view the touch-sensitive display control interface 108c located on the master control console 204. In this illustrative example display, the touch-sensitive display control interface 108c includes an endoscope illumination control component 108g to adjust the brightness settings on the endoscope illuminator that is the source of light 116b used to illuminate the surgical site. As shown, the control component image 620 includes both the endoscope illumination control component 108g and the surroundings of the endoscope illumination control component 108g. As a result, the operator of telesurgical robotic system 200 is able to locate and operate the endoscope illumination control component 108g located on the touch-sensitive display control interface 108c by observing the control component image 620 while concurrently observing the effects of his or her actions on the surgical site in real time in the surgical site image 610. It should be appreciated that use of the endoscope illumination control component 108g is merely illustrative of the various control components accessible through the touch-sensitive display control interface 108c. As discussed above, the touch-sensitive display control interface 108c may provide control components for control of various surgical functions that directly affect the surgical site such as suction, irrigation, tissue fusing functions, tissue stapling functions, endoscopic camera control and illumination functions, robotic master/slave control functions, etc. Other control components accessible through the touch-sensitive display control interface 108c may control functions that do not directly affect the surgical site such as operating room environment functions, patient data display functions, or any other function a surgeon may want to directly control while performing surgery. It should also be appreciated that in this example, use of the operator's hand to operate a control component located on the touch-sensitive display control interface 108c is merely illustrative of the many body parts of the operator that can be used to operate the many control components accessible to the operator of the telesurgical robotic system 200. The body part used by the telesurgical robotic system 200 operator depends on the physical relation between the operator's body and the control component. In some aspects, the control component captured within the field of view of the control component image capture device 102a is not the touch-sensitive display control interface 108c, and is positioned to be actuated by the operator's foot, the operator's knee(s), the operator's elbow(s), etc.

What is claimed is:

1. A control console comprising:
    a first input control operable by an operator and outside of a field of view of the operator;
    a display within the field of view of the operator; and
    a first image capture device;
    wherein:
        the first image capture device acquires a first image of a physical environment surrounding the first input control and at least part of the first input control; and
        the first image is output on the display.

2. The control console of claim 1, wherein the first image further comprises an image of at least a part of a body part of the operator used to operate the first input control.

3. The control console of claim 1, wherein the first image capture device comprises a stereoscopic image capture device.

4. The control console of claim 1, further comprising:
    a second input control operable by the operator and outside of the field of view of the operator;
    wherein the first image further comprises an image of at least part of the second input control.

5. The control console of claim 1, wherein a second image of a worksite captured by a second input capture device is output on the display.

6. The control console of claim 5, wherein the first image and the second image are simultaneously output on the display.

7. The control console of claim 1, wherein the display comprises a stereoscopic display.

8. The control console of claim 1, further comprising:
one or more sensors;
wherein:
the one or more sensors acquire information about the physical environment and the first input control;
a representation of the physical environment and the first input control are generated from the information; and
the representation is output on the display.

9. The control console of claim 1, wherein the first input control is configured to provide commands for a teleoperated device, an energy delivery device, or a surgical instrument.

10. The control console of claim 1, wherein the first input control is a pedal.

11. A method comprising:
acquiring, using a first image capture device, a first image of a first input control operable by an operator and outside of a field of view of the operator, the first image comprises an image of a least a part of the first input control; and
outputting the first image on a display within a field of view of the operator.

12. The method of claim 11, wherein the first image further comprises an image of at least a part of a body part of the operator used to operate the first input control.

13. The method of claim 11, wherein the first image capture device comprises a stereoscopic image capture device.

14. The method of claim 11, wherein the first image further comprises an image of at least part of a second input control operable by the operator and outside of the field of view of the operator.

15. The method of claim 11, further comprising:
acquiring a second image of a worksite captured by a second input capture device; and
outputting the second image on the display.

16. The method of claim 15, wherein the first image and the second image are simultaneously output on the display.

17. The method of claim 11, wherein the display comprises a stereoscopic display.

18. The method of claim 11, further comprising:
acquiring, using one or more sensors, information about the first input control and a physical environment of the first input control;
generating a representation of the physical environment and the first input control based on the information; and
outputting the representation on the display.

19. The method of claim 11, wherein the first input control is configured to provide commands for a teleoperated device, an energy delivery device, or a surgical instrument.

20. The method of claim 11, wherein the first input control is a pedal.

* * * * *

UNITED STATES PATENT AND TRADEMARK OFFICE
CERTIFICATE OF CORRECTION

| | |
|---|---|
| PATENT NO. | : 11,484,220 B2 |
| APPLICATION NO. | : 16/703497 |
| DATED | : November 1, 2022 |
| INVENTOR(S) | : Yiming Mei and Michael Ikeda |

It is certified that error appears in the above-identified patent and that said Letters Patent is hereby corrected as shown below:

On the Title Page

(63) Related U.S. Application Data:
Please delete "Continuation of application No. 14/785,726, filed as application No. PCT/US2014/035258 on Apr. 24, 2014, now Pat. No. 10,542,908." and insert --Continuation of application No. 14/785,726, filed on Oct. 20, 2015, now Pat. No. 10,542,908, which is a 371 of application No. PCT/US2014/035258, filed on Apr. 24, 2014.--.

Signed and Sealed this
Twentieth Day of December, 2022

Katherine Kelly Vidal
*Director of the United States Patent and Trademark Office*